(12) United States Patent
Choi et al.

(10) Patent No.: US 7,663,013 B2
(45) Date of Patent: Feb. 16, 2010

(54) SOLID ACID CATALYST FOR PRODUCING LIGHT OLEFINS AND PROCESS USING THE SAME

(75) Inventors: Sun Choi, Daejeon (KR); Deuk Soo Park, Gyeonggi-do (KR); Suk Joon Kim, Daejeon (KR); Ahn Seop Choi, Seoul (KR); Hee Young Kim, Daejeon (KR); Yong Ki Park, Daejeon (KR); Chul Wee Lee, Daejeon (KR); Won Choon Choi, Daejeon (KR); Sang Yun Han, Gyeongsangnam-do (KR); Jeong Ri Kim, Gyeongsangbuk-do (KR)

(73) Assignee: SK Energy Co., Ltd., Seoul (KR)

( * ) Notice: Subject to any disclaimer, the term of this patent is extended or adjusted under 35 U.S.C. 154(b) by 0 days.

(21) Appl. No.: 12/265,729

(22) Filed: Nov. 5, 2008

(65) Prior Publication Data

US 2009/0112035 A1 Apr. 30, 2009

Related U.S. Application Data

(62) Division of application No. 11/223,833, filed on Sep. 8, 2005.

(30) Foreign Application Priority Data

Sep. 10, 2004 (KR) .................... 10-2004-0072644

(51) Int. Cl.
*C07C 4/02* (2006.01)
*C10G 11/02* (2006.01)

(52) U.S. Cl. ............... 585/652; 585/651; 585/653; 208/114; 208/120.01; 208/122

(58) Field of Classification Search ........ 585/651–653; 208/114, 122, 120.01
See application file for complete search history.

(56) References Cited

U.S. PATENT DOCUMENTS

| 4,176,096 | A | * | 11/1979 | Patterson et al. | ............ 524/40 |
|---|---|---|---|---|---|
| 4,248,739 | A | * | 2/1981 | Vaughan et al. | ............ 502/63 |
| 5,110,685 | A | | 5/1992 | Cross et al. | |
| 5,171,921 | A | * | 12/1992 | Gaffney et al. | ............ 585/653 |
| 5,232,675 | A | * | 8/1993 | Shu et al. | ............ 423/328.2 |
| 5,343,655 | A | | 9/1994 | Miyakawa et al. | |
| 5,424,019 | A | | 6/1995 | Miyakawa et al. | |
| 5,424,135 | A | | 6/1995 | Murata et al. | |
| 6,146,739 | A | | 11/2000 | Itoh et al. | |
| 6,211,104 | B1 | * | 4/2001 | Shi et al. | ............ 502/67 |
| 6,342,153 | B1 | * | 1/2002 | Guan et al. | ............ 208/118 |
| 6,566,293 | B1 | * | 5/2003 | Vogt et al. | ............ 502/67 |
| 6,656,345 | B1 | * | 12/2003 | Chen et al. | ............ 208/120.01 |

* cited by examiner

*Primary Examiner*—In Suk Bullock
(74) *Attorney, Agent, or Firm*—Darby & Darby

(57) ABSTRACT

A porous solid acid catalyst for producing light olefins is prepared through pillaring and a solid state reaction of a raw material mixture. The catalyst is made of a porous material having a crystalline structure that is different from that of the raw material mixture. The catalyst exhibits excellent catalytic activity (i.e., conversion and selectivity) in the production of light olefins from hydrocarbon feeds such as full range naphthas.

9 Claims, 3 Drawing Sheets

SOLID ACID CATALYST FOR PRODUCING LIGHT OLEFINS AND PROCESS USING THE SAME

The present application is a divisional application of U.S. patent application Ser. No. 11/223,833, filed Sep. 8, 2005, which claims priority under 35 U.S.C. §119 to Korean Patent Application No. 10-2004-0072644 filed on Sep. 10, 2004. The content of the applications are incorporated herein by reference in their entirety.

INCORPORATION BY REFERENCE

The present application claims priority under 35 U.S.C. §119 to Korean Patent Application No. 10-2004-0072644 filed on Sep. 10, 2004. The content of the application is incorporated herein by reference in its entirety.

BACKGROUND OF THE INVENTION

1. Field of the Invention

The present invention relates to a solid acid catalyst and a process for producing light olefins from hydrocarbon feeds using the same. More particularly, the present invention pertains to a solid acid catalyst, which exhibits excellent selectivity to light olefins at a low temperature in comparison with any conventional techniques including steam cracking process, and a process of selectively producing light olefins from hydrocarbon feeds (typically, full range naphthas) using the same.

2. Description of the Related Art

Olefins, particularly, light olefins, such as ethylene or propylene, are extensively used in a petrochemical industry, and, typically, the light olefins are produced by conducting thermal cracking of naphthas in the presence of steam, i.e., steam cracking. Various modifications of the steam cracking technology have been attempted so as to cope with reaction conditions such as high temperature and reduction of retention time, and to optimize energy efficiency. However, it is not easy to improve energy efficiency using optimize energy efficiency. However, it is not easy to improve energy efficiency using only simple engineering technical modifications. Nowadays, the steam cracking process has consumed about 40% of the energy used in the total petrochemical industry. Accordingly, in consideration of economic efficiency and the reduction of environmental pollution, an improved process technology, that optimizes energy, saves raw materials, and minimizes the emission of carbon dioxide, is in demand. Typically, light naphthas are used as feeds, however since the light naphthas are more expensive than full range naphthas described later, there exists a limit in terms of economic efficiency. In the conventional steam cracking technology, it is not easy to control the composition of produced olefins, and a lot of heat energy is necessary because the required reaction temperature is on the order of 800-900° C., thus there is a need for improvement.

Furthermore, light olefin compounds may be produced through a FCC (fluid catalytic cracking) process. The FCC process is a catalytic cracking technology using a catalyst in the form of fine particle which behave like a fluid when they are aerated with steam, and is extensively known in the art. In particular, a DCC (deep catalytic cracking) technology is known as a process in which the FCC process is modified to improve the yield of olefins (mainly, propylene) instead of gasoline. Generally, the FCC process employs oils, such as vacuum residues, atmospheric residues, or gas oils, which are heavier than the full range naphthas desirably intended as feeds in the present invention.

With respect to the production of olefins, an olefin conversion process involving catalytic cracking has been suggested, in addition to the above-mentioned steam cracking and FCC processes. Most of these processes use an HZSM-5 as the solid acid catalyst, and related prior arts are as follows.

Japanese Patent Laid-Open No. Hei. 6-192135 discloses a catalytic cracking process (reaction conditions: a reaction temperature of 620-750° C. and a weight hourly space velocity (WHSV) of 1-200 $h^{-1}$) for producing ethylene and propylene from light naphthas containing $C_{2-12}$ paraffins (having a density of 0.683 g/cc; and a composition containing 42.7 wt % n-paraffins, 36.1 wt % i-paraffins, 0.1 wt % olefins, 14.0 wt % naphthenes, and 7.1 wt % aromatics; and the paraffins being composed of 0.1 wt % $C_3$, 5.2 wt % $C_4$, 18.7 wt % $C_5$, 19.0 wt % $C_6$, 15.2 wt % $C_7$, 13.5 wt % $C_8$, 6.1 wt % $C_9$, 0.1 wt % $C_{10}$, and 0.1 wt % $C_{11}$) in the presence of HZSM-5 or HZSM-11 catalyst having a $SiO_2/Al_2O_3$ molar ratio of 150-300. In particular, according to the above process, the conversion efficiency is about 93.6 wt % and the total amount of ethylene and propylene generated is 44.9 wt % under reaction conditions of 680° C. and a WHSV of 25 $h^{-1}$. However, HZSM-5 or HZSM-11 is used in a catalytic cracking reaction without being pelletized, and steam or inert gas is not introduced during the reaction, thus there is a possibility that the catalyst may be readily deactivated even though the initial activity is excellent. In this regard, an additional technology is required to shape the catalyst.

Meanwhile, Japanese Patent Laid-Open No. Hei. 6-199707 reports a catalytic cracking process for producing ethylene and propylene as main products from light naphthas having $C_{2-12}$ paraffins. In accordance with this prior art, a hydrogen-type zeolite ($SiO_2/Al_2O_3$=20-500) catalyst on which 100 ppm wt % iron (Fe) is supported is described to show good selectivity to light olefins. However, the zeolite is used in the catalytic cracking reaction without being pelletized, and steam or inert gas is not employed during the reaction, thus there is a possibility that the catalyst may be readily deactivated even though the initial activity is excellent.

U.S. Pat. No. 6,656,345 discloses catalytic cracking (reaction conditions: 400-700° C., WHSV: 1-1000 $h^{-1}$, and P: 0.1-30 atm) of hydrocarbons feed containing olefins (having a boiling point of 10-220° C. and containing 10-70 wt % olefins and 5-35 wt % paraffins) to produce propylene with a selectivity of 50% or higher and a ratio of propylene/butylene of 2-4. As such, the used catalyst is zeolite (e.g., zeolite having a structure, such as MFI, MEL, MTW, TON, MTT, FER, or MFS, and being exemplified by ZSM-21, ZSM-38, or ZSM-48) which has pores of about 7 Å and a ratio of silica/alumina of 200 or more.

U.S. Pat. No. 6,566,293 discloses a catalyst useful to produce light olefins. According to this patent, HZSM-5 zeolite, in which at least 10 wt % $P_2O_5$ is contained, and Y zeolite as main components (10-40 wt %) are mixed with silica (0-25 wt %) and amorphous alumina (about 10 wt %), pelletized through spray drying, and are sintered at 300-1000° C. to produce the catalyst. Furthermore, U.S. Pat. No. 6,521,563 discloses a method of producing a SAPO molecular sieve which contains 4-20 mol % Si, 40-55 mol % Al, and 30-50 mol % P and has an AEL structure, and its application to a catalyst for naphtha catalytic cracking.

WO 02/10313 A2 pertains to single component and mixed catalyst compositions which are used to selectively produce light olefins through steam cracking of hydrocarbons, such as n-hexane or n-octane, and discloses an extruded catalyst which comprises oxides of Al, Si and Cr, optionally oxides of alkaline metal (Na, K, Li or the like), and a binder (bentonite) and a method of producing the same. In this connection, the composition of catalyst as aforementioned contains 50-95 wt % $SiO_2$, 3-30 wt % $Al_2O_3$, 2-10 wt % $Cr_2O_3$, 0-18 wt % alkaline metal oxides, and 10-30 wt % binder.

Meanwhile, U.S. Pat. Nos. 4,248,739 and 4,176,090 disclose a layered compound (for example, bentonite expressed by the Formula $(Si_8)^{IV}(Al_4)^{VI}O_{20}(OH)_4$) that reacts with polymeric cationic hydroxy inorganic metal oxides, such as aluminum chlorohydrol expressed by the Formula $[Al_{26}(O)_8(OH)_{52}(H_2O)_{20}]^{10+}$, so as to achieve chemical pillaring, and is then dehydrated to form aluminum oxide pillars between layers of the layered compound, thereby a porous compound structure that is similar to zeolite is created. It is reported that the layered compound pillared through the above-mentioned method is more stable than a typical layered compound in hydrothermal property. However, there are difficulties in that reflux should be conducted for at least 24 hours and the hydrogen ion concentration (pH) should be precisely controlled during the reaction in order to produce the polymeric cationic hydroxy inorganic metal oxides.

U.S. Pat. No. 6,342,153 and Korean Patent Laid-Open No. 2003-0055172 disclose a method of producing a pillared clay catalyst, which is useful to thermal cracking of heavy oils, and the use of the same. This technology involves a production of porous material through pillaring by use of the layered compound. The method of producing the catalyst according to this technology is as follows. (i) Kaolin and HZSM-5 are modified with a rare earth metal ion and an alkaline earth metal ion, respectively and a pelletized catalyst is prepared using a spray dryer. (ii) Separately, polymeric cationic aluminum hydroxide complexes are prepared. (iii) The palletized catalyst produced in step (i) is pillared by use of the complexes of step (ii) at an appropriate pH to produce the catalyst. In this connection, the composition of the catalyst contains 30-75 wt % layered compound, 0-30 wt % HZSM-5 having a pentasil structure or Y-type zeolite, 10-40 wt % inorganic binder (oxides of Al, Si and/or Zr modified with polyethylene glycol), and 1-10 wt % modifying component (polyethylene glycol, and Mg, Al, K, P or Sn). In this technique, Daqing paraffins having a boiling point of 300-500° C. are catalytically and thermally cracked in the presence of a catalyst in accordance with the aforementioned method (reaction temperature: 700° C., catalyst/oil=10, a WHSV=10 $h^{-1}$, and $H_2O$/feeds=80 wt %), and $C_2$-$C_4$ olefins are produced at a maximum yield of 53 wt %.

U.S. Pat. No. 6,211,104 discloses a preparation method of catalyst applicable to a thermal cracking process for the production of light olefins, in which the pH of slurry consisting of 10-70 wt % layered compound (Kaolin), 5-85 wt % inorganic metal oxides (amorphous silica-alumina, alumina, silica, or pseudo-boehmite), and 1-50 wt % zeolite (0-25 wt % Y zeolite, and 75-100 wt % high silica zeolite with a pentasil structure which contains P and Al, P and Mg, or P and Ca) is controlled to 2-4, agitation is conducted at 20-80° C., pelletization is carried out using spray drying, and sintering is carried out at 450-650° C. At this time, the high silica zeolite comprises 2-8 wt % P and 0.3-3 wt % Al, Mg or Ca based on the weight of zeolite selected from the group consisting of ZSM-5, ZSM-8, and ZSM-11 having a $SiO_2/Al_2O_3$ molar ratio of 15-60. The Y zeolite refers to high silica Y zeolite in which 14 wt % or less rare earth metal oxides are included.

WO 01/04785 discloses a production of light olefins and aromatics in which a catalyst containing ZSM-5 and/or ZSM-11 zeolite comes into contact with $C_4$+ (compounds having 4 or more carbons) naphthas (boiling point: 27-221° C.). The catalyst is produced from raw material which comprises 5-75 wt % ZSM-5 and/or ZSM-11 zeolite having a $SiO_2/Al_2O_3$ ratio below 70, 20 wt % or less inorganic oxides (silica or clay), and 0.5-10 wt % P. When the $C_4$+ naphthas are catalytically cracked in the presence of the aforesaid catalyst (reaction temperature: 510-704° C., weight ratio of catalyst/feed: 0.01-30, steam/feed: 5-30 wt %, and WHSV: 1-20 $h^{-1}$), a ratio of ethylene/propylene (weight ratio) is at least 0.39, and a total amount of ethylene and propylene generated is about 25 wt % based on total products.

WO 03/064039 A1 pertains to a mixed catalyst for DCC (deep catalytic cracking) of n-hexane, n-octane, and light naphthas, which is useful for the selective production of light olefins such as ethylene, propylene, and BTX. In this prior art, the mixed catalyst comprises crystalline microporous silicate (for example, pentasil-type silicate) and mesoporous silica-alumina or $ZrO_2$, and $Al_2O_3$, $MoO_x$, $LaO_x$, $CeO_x$, a mixture thereof, or an inorganic binder, such as bentonite, is combined therewith. As such, a weight ratio of micropore/mesopore catalyst components is 0.25-4.0. Particularly, a weight ratio of $MoO_x/Al_2O_3$ is 0.5-1.5, and bentonite constitutes 9-25 wt % of the total mixed catalyst. However, it is believed that, it is not easy to control a micropore/mesopore distribution and the durability of the pelletized catalyst is poor because the mesoporous material is thermally unstable.

WO 01/81280 A1 discloses a method of producing ethylene and propylene. In the method, a zeolite (TON, MTT) catalyst, which has a pore size index of 23-25, no one-dimensional channels cross-linked with each other, and a diameter of 4.4-4.5 Å, comes into contact with one or more $C_4$-$C_9$ olefins (e.g., a mixture of butane and butene) and is heated. According to the method, a fixed bed reaction is conducted under conditions of a temperature of 450-750° C., pressure of 0.5-10 atm, and a WHSV of 0.5-1000 $h^{-1}$. According to this prior art, in case that the reaction is carried out using butene as a feed at 525° C. and a WHSV of 2.5 $h^{-1}$ for 202 hours, the total amount of ethylene and propylene is 91.7 wt %, and a ratio of propylene/ethylene is 4.8.

WO 01/04237 A2 discloses a production of light olefins, in which hydrocarbons containing at least 50 wt % $C_4$-$C_7$ aliphatic hydrocarbons are used as feeds and come into contact with ZSM-5 and/or ZSM-11 having a $SiO_2/Al_2O_3$ ratio over 300 and containing P. In detail, the catalyst used in this prior art comprises 5-75 wt % zeolite, 25-95 wt % matrix such as silica, alumina and clay, and 0.5-10 wt % P. The reaction conditions include a temperature of 510-704° C., a pressure of 0.1-8 bar, a ratio of catalyst/feed of 0.1-10 (weight ratio), and a space velocity of 1-20 $h^{-1}$. At this time, the total amount of ethylene and propylene generated is 20 wt % of total products, and a ratio of propylene/ethylene is at least 3.

U.S. Pat. No. 5,171,921 discloses a method for selectively producing $C_2$-$C_5$ olefins. According to the aforementioned method, $C_3$-$C_{20}$ hydrocarbons, which is a mixture of paraffins and olefins, are catalytically cracked (reaction temperature: 550-600° C., and WHSV: 10-1000 $h^{-1}$) in the presence of a pelletized catalyst which comprises 10-25 wt % ZSM-5 containing 1-3 wt % P and having a Si/Al ratio of 20-60, and a binder such as silica, Kaolin, and bentonite. It is reported that the performance of ZSM-5 is improved through steam-activation at 500-700° C., and that the conversion and the total amount of ethylene and propylene are 60% and 60 wt %, respectively, when 2-butene is catalytically cracked (reaction temperature: 600° C., and WHSV: 366 $h^{-1}$).

U.S. Pat. No. 5,232,675 and Korean Patent Application No. 1996-7000207 disclose a method of producing a pentasil-type high silica zeolite catalyst in which $RE_2O_3$ is 0.01-0.30, $Na_2O$ is 0.4-1.0 and a ratio of $SiO_2/Al_2O_3$ is 20-60. According to this patent, the disclosed catalyst is better than HZSM-5 in hydrothermal stability.

WO 2004/037951 A1 discloses a method of producing a rare earth element-containing zeolite ($SiO_2/Al_2O_3$=25-800) catalyst (such as La—Mn/HZSM-5, La—Mn/HZSM-5 and P—La—Mn/HZSM-5) having a pentasil structure, in which manganese (an atomic ratio of manganese to aluminum in zeolite is 0.1-20), zirconium (an atomic ratio of zirconium to aluminum in zeolite is 4-20), and/or phosphorus (0.1-5 wt %) are contained. This patent mentions that the catalyst shows excellent catalytic cracking performance in the presence of steam at a relatively low temperature, and that when n-butane is catalytically cracked at 650° C. and a WHSV of 50 $h^{-1}$, the conversion is 90.2%, the total amount of ethylene and propylene generated is 51.3 wt %, and the ratio of ethylene/propylene is 2.35. According to the patent, ethylene is generated in a relatively larger amount.

In the light of foregoing, the preparation of the catalysts known in the conventional catalytic cracking arts, can roughly be classified into two categories.

As for a first method, HZSM-5 having a MFI structure or HZSM-5 modified with P as a main component is physically mixed with an inorganic oxide binder to prepare a pelletized catalyst. However, only ZSM-5 participates in the catalytic cracking, and the binder physically mixed therewith does not show the catalytic activity. Moreover, in order to improve catalytic cracking performance, it is required to control a relative amount of the main component of the catalyst or artificially introduce a component serving as micropores or mesopores, depending on the compositional characteristics of naphthas (for example, when the naphthas become heavy). Hence, it is difficult to optimize preparation conditions of the pelletized catalyst in consideration thereof.

In a second method, in order to produce a pelletized catalyst, pillared layered material is added with HZSM-5 and Y-zeolite, and then an inorganic oxide binder and an additive are introduced thereto. The main component of the catalyst is zeolite having a pore size of 5-6 Å and a three dimensional structure, which is represented by HZSM-5.

However, the catalyst has a drawback in that much time is taken due to the complexity of the synthesis procedures, and reproducibility is poor when the catalyst is commercially produced.

As with the prior arts as discussed above, heavy oils (vacuum residues, atmospheric residues, gas oils and the like), or light oils containing a predetermined content of olefins are typically used as feeds. If heavy oils are used as the feed, undesirably, the yield of light olefins is low. On the other hand, if light oils are used as the feed, a desired yield of light olefins is plausible only when the oils contain the specific olefin content or more.

SUMMARY OF THE INVENTION

To solve the problems encountered in the prior arts, the present inventors have developed a novel porous solid acid catalyst which exhibits various advantages in comparison with the conventional HZSM-5 zeolite-based catalyst and an excellent conversion performance of hydrocarbons fraction (represented by full range naphthas, especially the full range naphthas having $C_{2-12}$ hydrocarbons) into light olefins (e.g., ethylene and propylene), and which can be prepared in the simple procedure. In addition, there has been developed an improved process for producing light olefins with good efficiency and selectivity by use of such a novel catalyst even at a low temperature in comparison with the conventional techniques including steam cracking. More specifically, the present invention is based on the unexpected finding that a porous material, which is prepared through (i) a pillaring reaction and (ii) a solid state reaction of a raw material mixture having specific components and compositional ratio, has properties (e.g., crystalline structure) that are apparently different from those of the raw mixture, and that if it is employed as a catalyst for producing light olefins from the hydrocarbons fraction, high yield and selectivity can be attained.

Accordingly, an object of the present invention is to provide a solid acid catalyst showing selective conversion performance of hydrocarbons fraction into light olefins.

Another object of the present invention is to provide a method of preparing a solid acid catalyst for producing light olefins, which is advantageous in that commercial preparation is readily achieved due to simplicity of synthetic procedure.

Still another object of the present invention is to provide a process of producing light olefins from hydrocarbons fraction in the presence of the aforesaid solid acid catalyst.

According to a first aspect of the present invention, there is provided a porous solid acid catalyst for producing light olefins, which comprises a product of (i) pillaring reaction and (ii) solid state reaction through heat treatment of a raw material mixture, and has a crystalline structure represented by an X-ray diffraction (XRD) pattern in Table 1. The raw material mixture comprises 42.0-60.0 wt % HZSM-5 having Si/Al molar ratio of 15-300, 12.0-38.0 wt % layered compound, 1.0-20.0 wt % $Al_2O_3$, 1.0-4.0 wt % $P_2O_5$, 10.0-15.0 wt % $SiO_2$, and 0.5-2.5 wt % $B_2O_3$ based on an oxide form.

TABLE 1

| 2θ | Relative intensity |
|---|---|
| 7.899 | 81.4 |
| 8.760 | 48.1 |
| 14.76 | 15.3 |
| 19.92 | 15.2 |
| 20.36 | 21.2 |
| 23.06 | 100 |
| 23.88 | 59.7 |
| 24.36 | 24.5 |
| 25.60 | 15.3 |
| 25.82 | 18.4 |
| 26.60 | 22.2 |
| 26.86 | 20.8 |
| 29.90 | 22.5 |
| 45.00 | 17.5 |
| 45.48 | 17.4 |

According to a second aspect of the present invention, there is provided a preparation method of a porous solid acid catalyst for producing light olefins, which includes the steps of:

conducting a pillaring reaction of a raw material mixture comprising 42.0-60.0 wt % HZSM-5 having Si/Al molar ratio of 15-300, 12.0-38.0 wt % layered compound, 1.0-20.0 wt % $Al_2O_3$ as a pillaring agent, 1.0-4.0 wt % $P_2O_5$, 10.0-15.0 wt % $SiO_2$, and 0.5-2.5 wt % $B_2O_3$ based on an oxide form, in water to prepare an aqueous slurry containing the pillared product;

pelletizing the aqueous slurry to form a pelletized catalyst; and conducting a solid state reaction of the pelletized catalyst under a heat treatment condition sufficient to give a crystalline structure having an XRD pattern of Table 1, to the pelletized catalyst.

According to a third aspect of the present invention, there is provided a process for producing light olefins, which includes the steps of:

providing hydrocarbons fraction as a feed;

transferring the feed into a reaction zone including at least one reactor to react the feed in the presence of the above catalyst; and separating light olefins from the effluent of said reaction zone to recover light olefins.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
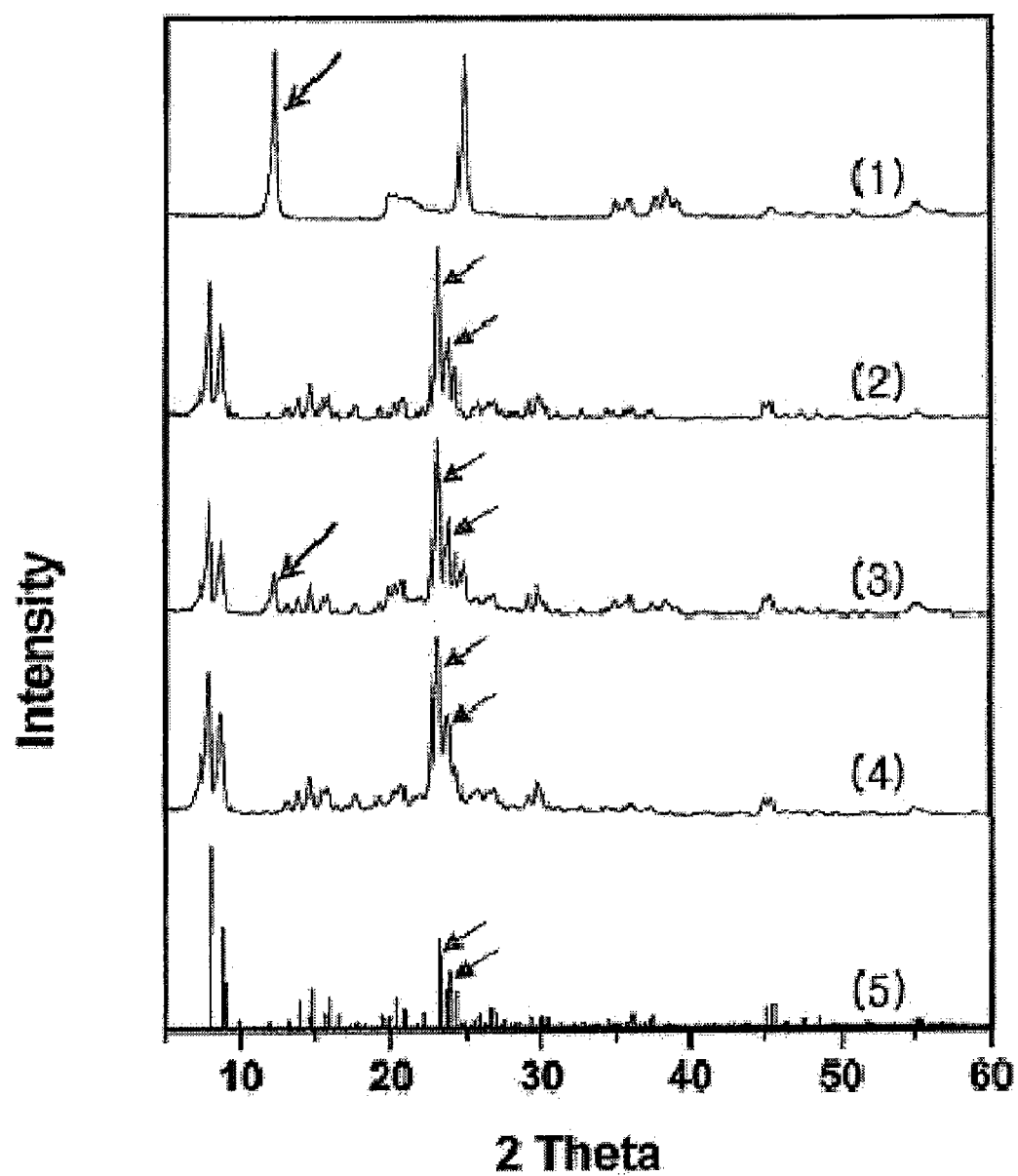
FIG. 1 illustrates XRD patterns of a layered compound, Kaolin (1) and HZSM-5 (2) which are raw materials used to produce a catalyst according to the present invention, a pelletized catalyst before heat treatment (3), a pelletized catalyst after heat treatment, Example 2 (4), and ZSM-5 cited from Joint Committee of Powder Diffraction (JCPDS) card No. 45-0133 (5), respectively.

Hereinafter, a detailed description will be given of the present invention, referring to the accompanying drawings.

As described above, with respect to a porous solid acid catalyst for producing light olefins, a catalytically active component (i.e., HZSM-5) of a raw material mixture containing 42.0-60.0 wt % HZSM-5 having a Si/Al molar ratio of 15-300, 12.0-38.0 wt % layered compound, 1.0-20.0 wt % $Al_2O_3$, 1.0-4.0 wt % $P_2O_5$, 10.0-15.0 wt % $SiO_2$, and 0.5-2.5 wt % $B_2O_3$ based on an oxide form, is subjected to a solid state reaction in conjunction with a pillared layered compound, and is converted into a porous material having properties (crystalline structure) that are completely different from an original form thereof. In case that it is applied as a catalyst to the production of light olefins, various advantages are assured in yield and selectivity. According to the present invention, the acidity, and the compositional and structural characteristics of the catalyst are appropriately chosen and controlled using the following techniques:

(1) a technique in which the layered compound (for example, Kaolin, bentonite, or saponite) in the raw material for the catalyst is pillared by use of a pillaring-binding agent, pelletized along with the HZSM-5 zeolite which is the main component, and subjected to the solid state reaction;

(2) a technique for adding an additive, such as boron (B), to control concentrations and intensities of acidic sites of the solid acid; and (3) a technique in which a specific amount of inorganic metal oxide as a binder is employed to prepare a pelletized catalyst and which at the same time assures excellent activity and prevents physical destruction of the catalyst even during the conversion (for example, catalytic cracking) of hydrocarbons fraction in a high temperature steam atmosphere.

A description of the catalyst according to the present invention is not limited to a specific theory. However, it is supposed that, when the raw mixture containing HZSM-5 and the pillared layered compound is pelletized and heat treated under specific conditions, metal oxide pillars are firmly formed between layers of the layered compound, thus porosity is developed and a solid state reaction occurs between particles, thereby the catalyst has properties (particularly, X-ray diffraction structure) that are demonstrably different from those of components constituting the raw material, particularly the main component (i.e., HZSM-5).

As described above, the porous solid acid catalyst according to the present invention, after being subjected to the solid state reaction, has the XRD pattern shown in the following Table 1, and is also different in crystalline structure from each of HZSM-5, the layered compound and a physical mixture thereof used in the raw material mixture. Furthermore, a specific surface area of the resulting catalyst is preferably 200-400 $m^2/g$, and more preferably 200-300 $m^2/g$.

TABLE 1

| $2\theta$ | Relative intensity |
|---|---|
| 7.899 | 81.4 |
| 8.760 | 48.1 |
| 14.76 | 15.3 |
| 19.92 | 15.2 |
| 20.36 | 21.2 |
| 23.06 | 100 |
| 23.88 | 59.7 |
| 24.36 | 24.5 |
| 25.60 | 15.3 |
| 25.82 | 18.4 |
| 26.60 | 22.2 |
| 26.86 | 20.8 |
| 29.90 | 22.5 |
| 45.00 | 17.5 |
| 45.48 | 17.4 |

In accordance with an embodiment, the catalyst is prepared as follows: the pillaring of a layered compound in the raw mixture having the specific composition; the shaping of the pillaring-subjected raw mixture; and the solid state reaction of the pelletized catalyst under heat treatment conditions sufficient to achieve the crystalline structure having the XRD pattern as set forth above. An exemplified method is explained in detail, below.

(1) An aqueous pillaring-binding solution, in which an aluminum compound as source of alumina ($Al_2O_3$) and a phosphorus compound as source of phosphorus pentoxide ($P_2O_5$) are controlled in the predetermined ratio, is prepared. As such, the aluminum compound acts as a pillaring agent to form pillar structures between layers of the layered compound which is one of the raw materials described later. As binding agent, the phosphorus compound functions to smoothly combine HZSM-5 (as a main component) with the layered compound (as an auxiliary component). In this connection, a molar ratio of $Al_2O_3/P_2O_5$ is preferably controlled in the range of about 0.7-1.4, and more preferably on the order of 1.0 as a factor affecting the strength of the catalyst to be pelletized. It is preferred that they are mixed with each other in water (e.g., distilled water) under stirring to result in a homogeneous aqueous solution. Optionally, it is preferred to allow the resultant solution to stand at room temperature for about 10-15 hours to achieve aging of the aqueous pillaring-binding solution. The aluminum compound (as the source of $Al_2O_3$) is typically in the form of aluminum salt, for example $Al(NO_3)_3 \cdot 9H_2O$, $Al_2(SO_4)_3 \cdot 18H_2O$, $AlCl_3 \cdot 6H_2O$, or a mixture thereof. Most preferable is $Al(NO_3)_3 \cdot 9H_2O$. Meanwhile, the phosphorus compound (as the source of $P_2O_5$) is typically phosphoric acid or a salt thereof, and is exemplified $H_3PO_4$, $(NH_4)_2HPO_4$, or a mixture thereof. $H_3PO_4$ is most preferable.

(2) Separately, HZSM-5, a layered compound and a silicon compound is admixed with each other in water (preferably, distilled water) to give a slurry. It is preferable that mixing be conducted for about 5-10 hours to prepare the homogeneous mixture. It is also preferable that a solid content in the slurry be controlled within a range from 20.0 to 60.0 wt %.

As for HZSM-5, depending on the distribution and concentration of solid acid, it is chosen among ones ranging within about 15-300 and preferably about 25-80 in Si/Al molar ratio. The general properties thereof are well known in the art. Preferably, the specific surface area is about 350-430 $m^2/g$ and the pore size is about 5-6 Å.

As a layered compound, either natural layered compounds or chemically synthesized layered compounds can be used. Among them, Kaolin, bentonite, saponite, or a mixture thereof is used with preference. Kaolin is most preferably used in the present invention.

Furthermore, a source of silica used as an auxiliary binder is not specifically limited, and any silicon compounds (e.g., Ludox silica sol AS-40, Ludox silica sol HS-40, Ludox silica sol HS-30 or a mixture thereof) known in the art may be used. Ludox silica sol AS-40 is most preferable.

(3) The solution and the slurry obtained in the steps (1) and (2), respectively, are mixed with each other, and a boron compound, which is the source of boron oxide ($B_2O_3$), preferably a boric acid aqueous solution (for example, having a concentration of about 5.0-10.0 wt %), is added thereto in order to prepare the homogeneous slurry. In this respect, the boron oxide is inserted into defect sites of HZSM-5 and the layered compound during the subsequent solid state reaction so as to appropriately control the acidic sites of the final catalyst. The mixing is preferably conducted for a time sufficient to cause a pillaring reaction. More preferably, the mixing is conducted with agitation (particularly, vigorous agitation) for about 10-15 hours. The time point when the boric acid solution is added is not specifically limited, but it is preferable that such addition is performed while the solution being mixed with the slurry. In the step (3), the pillaring reaction occurs between the layers of the layered compound by the aluminum compound contained in the aqueous pillaring-binding solution, and it is preferable to conduct agitation so that the pillaring reaction occurs sufficiently, as described above. Schematic description of the pillaring reaction is disclosed in U.S. Pat. Nos. 6,342,153 and 5,614,453, which are incorporated for reference herein.

(4) The aqueous slurry prepared in step (3) is pelletized to form a catalyst having a predetermined shape. Preferably, fine spheres having a uniform size (for example, about 50-80 μm) are pelletized through spray drying. As described later, it is considered that the properties of the respective components (such as HZSM-5 and the layered compound) constituting the raw mixture are physically mixed with each other in the pelletized catalyst.

(5) According to the present invention, the pelletized catalyst is subjected to a solid state reaction under heat treatment so as to have the above-mentioned XRD pattern, resulting in a structure that is different from those of the components constituting the raw material. In addition, it is believed that, during the heat treatment, the respective sources of alumina, silica, phosphorus pentoxide and boron oxide are converted into oxide forms thereof, any impurities are removed, the porosity is increased to optimize the performance of the catalyst, and the physical strength of the pelletized catalyst is improved. A preferred aspect of the heat treatment consists of two steps, and the steps are as follows.

The first heat treatment step is conducted in an inert atmosphere (for example, a nitrogen atmosphere) at a temperature of about 450-600° C., and preferably about 500° C., and a preferred heat treatment time is about 3-5 hours. In the first heat treatment step, the impurities contained in pores of a porous molecular sieve are removed to develop pores, and the distances between the particles is so close that an formation of metal oxide pillars between the layers of layered pillared compound and a binding reaction between HZSM-5 and the layered compound are efficiently carried out in the subsequent second heat treatment step.

The second heat treatment step is conducted in the presence of oxygen (preferably, in an air atmosphere) at a temperature of about 550-700° C., and preferably about 650° C., and a preferred heat treatment time is about 3-5 hours. Through this heat treatment step, the final pelletized catalyst is created. According to the present invention, it is desirable that the temperature of the second heat treatment is higher than that of the first heat treatment preferably by about 50-200° C., more preferably by about 100-150° C. The pillaring of the layered compound in the pelletized catalyst subjected to the first heat treatment step is completed in the second heat treatment step, and thus the oxide pillars are firmly formed between the layers, resulting in conversion into the porous material. Furthermore, the boron component used as the additive is inserted into the defect sites of HZSM-5 and the layered compound so as to appropriately control acidic sites of the pelletized catalyst, and the inorganic binder and other components are sintered so as to assure high physical strength. Under a high temperature atmosphere, it is believed that HZSM-5 acts as a seed to convert the structure of the pillared layered compound into a zeolite-like crystalline structure. After the solid state reaction is completed, the resulting product is a porous material whose properties (e.g., an XRD pattern) are not identical to those of HZSM-5 as the raw material.

The above description can be confirmed by an XRD pattern shown in FIG. 1. In the drawing, (1) and (2) respectively denote the layered compound (Kaolin) and HZSM-5 zeolite used as the raw materials. (3) denotes a sample which is prepared by mixing the raw materials having the predetermined composition and shaping the resulting mixture by use of spray drying, and in which properties of (1) and (2) are physically mixed with each other.

Meanwhile, (4) shows a pelletized sample which has been subjected to the two-step heat treatment as set forth above, and has a pattern where the peak (especially, 2θ=12.5°) caused by the layered compound of (1) disappears and an overall X-ray diffraction pattern is different from the typical one of ZSM-5 (5). The reason for this seems to be because the material having a ZSM-5 crystalline structure is modified during the high temperature heat treatment of the pelletized sample so as to have a crystalline structure that is different from that of ZSM-5. From careful examination of the X-ray diffraction structure, it can be seen that, in the pelletized sample before the heat treatment, a peak which centers at 2θ s of 23.0° and 23.8° is divided into two (3) unlike the X-ray diffraction structure of the sample after the heat treatment.

As well, from X-ray diffraction structures obtained before and after the heat treatment, it is observed that intensities of two peaks (2θ=7.9° and 8.8°) at 2θ of 10° or less in the samples (2) and (3) obtained before the heat treatment are both increased by about 20% (4) after the heat treatment (on the assumption that the intensity of a peak at 2θ of 23.0° is 100). This indicates that a frame structure prior to the heat treatment corresponds to ZSM-5, but is converted into the other type of structure after the heat treatment.

According to the present invention, the raw material for producing the catalyst should be adjusted to have the composition comprising 42.0-60.0 wt % HZSM-5 having Si/Al molar ratio of 15-300, 12.0-38.0 wt % layered compound, 1.0-20.0 wt % $Al_2O_3$, 1.0-4.0 wt % $P_2O_5$, 10.0-15.0 wt % $SiO_2$, and 0.5-2.5 wt % $B_2O_3$ based on an oxide form to be converted by the heat treatment process. If the composition deviates from the above range, an X-ray diffraction structure is formed so that a crystalline phase corresponding to a structure of HZSM-5 or an amorphous phase generated due to the destruction of a structure of the layered compound are physically mixed, or a third component generated during the solid state reaction is mixed therewith, as confirmed by Examples and Comparative Examples. Although U.S. Pat. No. 6,211,104 discloses a preparation method of a pelletized catalyst which comprises 10-70 wt % layered compound, 5-85 wt % inorganic oxide, and 1-50 wt % zeolite (HZSM-5), it cannot be considered to relate to the creation of a novel crystalline structure, unlike the present invention.

According to the present invention, the porous material is useful as a catalyst for selective production of light olefins from hydrocarbons fraction, preferably full range naphthas, more preferably full range naphthas having $C_{2-12}$ hydrocarbons. In this regard, the feasible type of reaction to be involved therein will be catalytic cracking reaction. Among the hydrocarbons used as feed, the full range naphthas are different from costly light naphthas used in a steam cracking process for the production of light olefins, a raw material containing olefins used in the conventional catalytic cracking processes, and $C_{20-30}$ heavy oils which have been generally used in the FCC process. In the present process, the full range naphthas are preferably employed as a feed in the economic standpoint, even though the use of other hydrocarbon fractions is possible. The various advantages obtained from the use of full range naphthas are owing to the excellent catalytic performance of the catalyst as provided by the present invention.

Typically, the full range naphtha refers to a hydrocarbons fraction containing $C_{2-12}$ hydrocarbons directly obtained from a crude oil refining process, and comprises paraffins (n-paraffins and i-paraffins), naphthenes, aromatic compounds, and the like. In some cases, a certain amount of olefins may be further present therein. Generally, when the paraffin-content in the full range naphthas is high, the full range naphthas have a light characteristic, while when the paraffin-content is low, the full range naphthas have a heavy characteristic. In choosing the feed, the full range naphthas which have the total paraffin (i.e., n-paraffins and i-paraffins) content of preferably 60-90 wt %, more preferably 60-80 wt %, and most preferably 60-70 wt % may be used depending on yield, economic efficiency and the like. Furthermore, olefins may be contained in an amount of 20 wt % or less, preferably 10 wt % or less, and more preferably 5 wt % or less. The exemplified composition of the feed available in the present invention is described in the following Table 2 (unit: wt %).

Additionally, the feed to be used may be a mixture of the full range naphthas and $C_{4-5}$ hydrocarbons recycled after light olefins and heavy products are separated from an effluent of the reaction zone.

TABLE 2

|  | n-paraffin | i-paraffin | Naphthene | Aromatic | Olefin |
|---|---|---|---|---|---|
| Naphtha 1 | 33.5% | 33.0% | 19.7% | 13.8% | 0.0% |
| Naphtha 2 | 35.7% | 48.7% | 11.2% | 3.2% | 1.2% |

In the present invention, at least one reactor may be provided in the reaction zone. The type of reactor is not specifically limited, but a fixed bed reactor or a fluidized bed reactor may be used with preference. The feed is subjected to a conversion reaction (e.g., catalytic cracking) in the presence of the catalyst of the present invention within the reactor, and are thus converted into light olefins.

Generally, the reaction performance significantly depends on a reaction temperature, a space velocity, and a weight ratio of hydrocarbons (e.g., naphtha)/steam. In this connection, in order to minimize energy consumption, it is required to set a reaction condition so that the temperature is as low as possible, the conversion and the amount of olefins generated are optimized, and deactivation of the catalyst due to the generation of coke is minimized. In a preferred aspect of the present invention, the reaction temperature is about 500-750° C., preferably about 600-700° C., and more preferably about 610-680° C. Furthermore, the weight ratio of hydrocarbons/steam is about 0.01-10, preferably about 0.1-2.0, and more preferably about 0.3-1.0.

If the fixed bed reactor is used, the space velocity is about 0.1-20 $h^{-1}$, preferably about 0.3-10 $h^{-1}$, and more preferably about 0.5-4 $h^{-1}$. On the other hand, if the fluidized bed reactor is used, a weight ratio of catalyst/hydrocarbons is about 1-50, preferably about 5-30, and more preferably about 10-20, and a retention time of hydrocarbons is about 0.1-600 sec, preferably about 0.5-120 sec, and more preferably about 1-20 sec.

According to the present invention, the amount of light olefins (i.e., the sum of ethylene and propylene) in the effluent of the reaction zone is preferably about 40 wt % or more, more preferably about 45 wt % or more, and most preferably about 47 wt % or more. As such, a weight ratio of ethylene/propylene is about 0.5-1.5.

A better understanding of the present invention may be obtained through the following examples and comparative examples which are set forth to illustrate, but are not to be construed as the limit of the present invention.

EXAMPLE 1

(1) 23.303 g of 85.0 wt % phosphoric acid were homogeneously mixed with 125.63 g of 60.2 wt % $Al(NO_3)_3.9H_2O$ solution, and aged at room temperature for 12 hours.

(2) 75.2 g of HZSM-5 (Zeolyst International Inc.) having Si/Al molar ratio of 25 and a specific surface area of 400 $m^2/g$ and 69.6 g of Kaolin (Aldrich Co., Ltd.) were added to 120 g of distilled water, and then agitated at 12,000 rpm for 10 hours. While the viscosity of slurry was controlled during the agitation, 56.4 g of Ludox silica sol AS-40 (Aldrich Co., Ltd.) were added thereto. After the agitation was stopped, 50.0 g of mixed solution (1) and 55.0 g of 9.1 wt % boric acid solution were added thereto, and agitated again for 11 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A Brunauer-Emmett Teller (BET) specific surface area of the resulting catalyst was measured, and found to be about 200 $m^2/g$. The composition of raw material used is shown in the following Table 3.

EXAMPLE 2

The procedure of Example 1 was repeated to produce a catalyst, with the exception that the composition of raw material was changed as shown in the following Table 3. The particle size was about 50-80 μm, and the BET specific surface area was about 270 m²/g.

EXAMPLE 3

A catalyst was prepared in the same procedure as in Example 2, and the present example was conducted in order to evaluate the effect according to the type of full range naphthas.

COMPARATIVE EXAMPLE 1

Kaolin (Aldrich Co., Ltd.) was subjected to first heat treatment in a nitrogen atmosphere at 500° C. for 3 hours, and then second heat treatment in an air atmosphere at 650° C. for 3 hours to produce a catalyst. A BET specific surface area was about 20 m²/g.

COMPARATIVE EXAMPLE 2

42.0 g of Kaolin (Aldrich Co., Ltd.) were added to 30.0 g of distilled water, and then agitated at 12,000 rpm for 10 hours. While the viscosity of slurry was controlled during the agitation, 33.8 g of Ludox silica sol AS-40 were added thereto. After the agitation was stopped, 30 g of solution (1) prepared in Example 1 and 22 g of 9.1 wt % boric acid solution were added thereto, and agitated again for 5 hours to give a homogeneous slurry. A pelletized catalyst was produced from the slurry using a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 50 m²/g. The composition of raw material used is shown in the following Table 3.

COMPARATIVE EXAMPLE 3

27.0 g of HZSM-5 (Zeolyst International Inc.) having Si/Al molar ratio of 25 and a specific surface area of 400 m²/g and 35.0 g of Kaolin (Aldrich Co., Ltd.) were added to 45.0 g of distilled water, and then agitated at 12,000 rpm for 10 hours. While the viscosity of slurry was controlled during the agitation, 17.0 g of Ludox silica sol AS-40 were added thereto. After the agitation was stopped, 25.2 g of 60.2 wt % Al(NO$_3$)$_3$.9H$_2$O solution were added thereto, and agitated again for 5 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 150 m²/g. The composition of raw material used is shown in the following Table 3.

COMPARATIVE EXAMPLE 4

17.0 g of HZSM-5 (Zeolyst International Inc.) having Si/Al molar ratio of 25 and a specific surface area of 400 m²/g and 27.8 g of Kaolin (Aldrich Co., Ltd.) were added to 40.0 g of distilled water, and then agitated at 12,000 rpm for 10 hours. While the viscosity of slurry was controlled during the agitation, 22.6 g of Ludox silica sol AS-40 were added thereto. After the agitation was stopped, 20 g of solution (1) prepared in Example 1 and 16.5 g of 9.1 wt % boric acid solution were added thereto, and agitated again for 5 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 150 m²/g. The composition of raw material used is shown in the following Table 3.

COMPARATIVE EXAMPLE 5

58.0 g of HZSM-5 (Zeolyst International Inc.), having Si/Al molar ratio of 25 and a specific surface area of 400 m²/g, and 52.6 g of Kaolin (Aldrich Co., Ltd.) were added to 80.0 g of distilled water, and then agitated at 12,000 rpm for 10 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 240 m²/g. The composition of raw material used is shown in the following Table 3.

COMPARATIVE EXAMPLE 6

13.2 g of HZSM-5 (Zeolyst International Inc.) having Si/Al molar ratio of 25 and a specific surface area of 400 m²/g and 29.0 g of Kaolin (Aldrich Co., Ltd.) were added to 25.0 g of distilled water, and then agitated at 12,000 rpm for 10 hours. While the viscosity of slurry was controlled during the agitation, 12.5 g of Ludox silica sol AS-40 were added thereto. After the agitation was stopped, 102 g of solution (1) prepared in Example 1 and 27.5 g of 9.1 wt % boric acid solution were added thereto, and agitated again for 5 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 80 m²/g. The composition of raw material used is shown in the following Table 3.

COMPARATIVE EXAMPLE 7

26.4 g of HZSM-5 (Zeolyst International Inc.) having Si/Al molar ratio of 25 and a specific surface area of 400 m²/g and 97.5 g of Kaolin (Aldrich Co., Ltd.) were added to 90 g of distilled water, and then agitated at 12,000 rpm for 10 hours.

While the viscosity of slurry was controlled during the agitation, 78.94 g of Ludox silica sol AS-40 were added thereto. After the agitation was stopped, 70 g of solution (1) prepared in Example 1 and 33.0 g of 9.1 wt % boric acid solution were added thereto, and agitated again for 5 hours to give a homogeneous slurry. A pelletized catalyst was produced from the slurry by use of a spray drier (MH-8 manufactured by ME HYUN Engineering Co., Ltd.) (such that particle sizes ranged from 50 μm to 80 μm). Subsequently, the pelletized catalyst was subjected to first heat treatment in a nitrogen atmosphere at 500° C. for 3 hours, and then second heat treatment in an air atmosphere at 650° C. for 3 hours to produce a catalyst. A BET specific surface area of the resulting catalyst was measured, and found to be about 80 m²/g. The composition of raw material used is shown in the following Table 3.

COMPARATIVE EXAMPLE 8

HZSM-5 (Zeolyst International Inc.) having Si/Al molar ratio of 25 and a specific surface area of 400 m²/g was subjected to first heat treatment in a nitrogen atmosphere at 500° C. for 3 hours, and then second heat treatment in an air atmosphere at 650° C. for 3 hours to produce a catalyst. A BET specific surface area was about 400 m²/g after the heat treatment.

Figure 3:
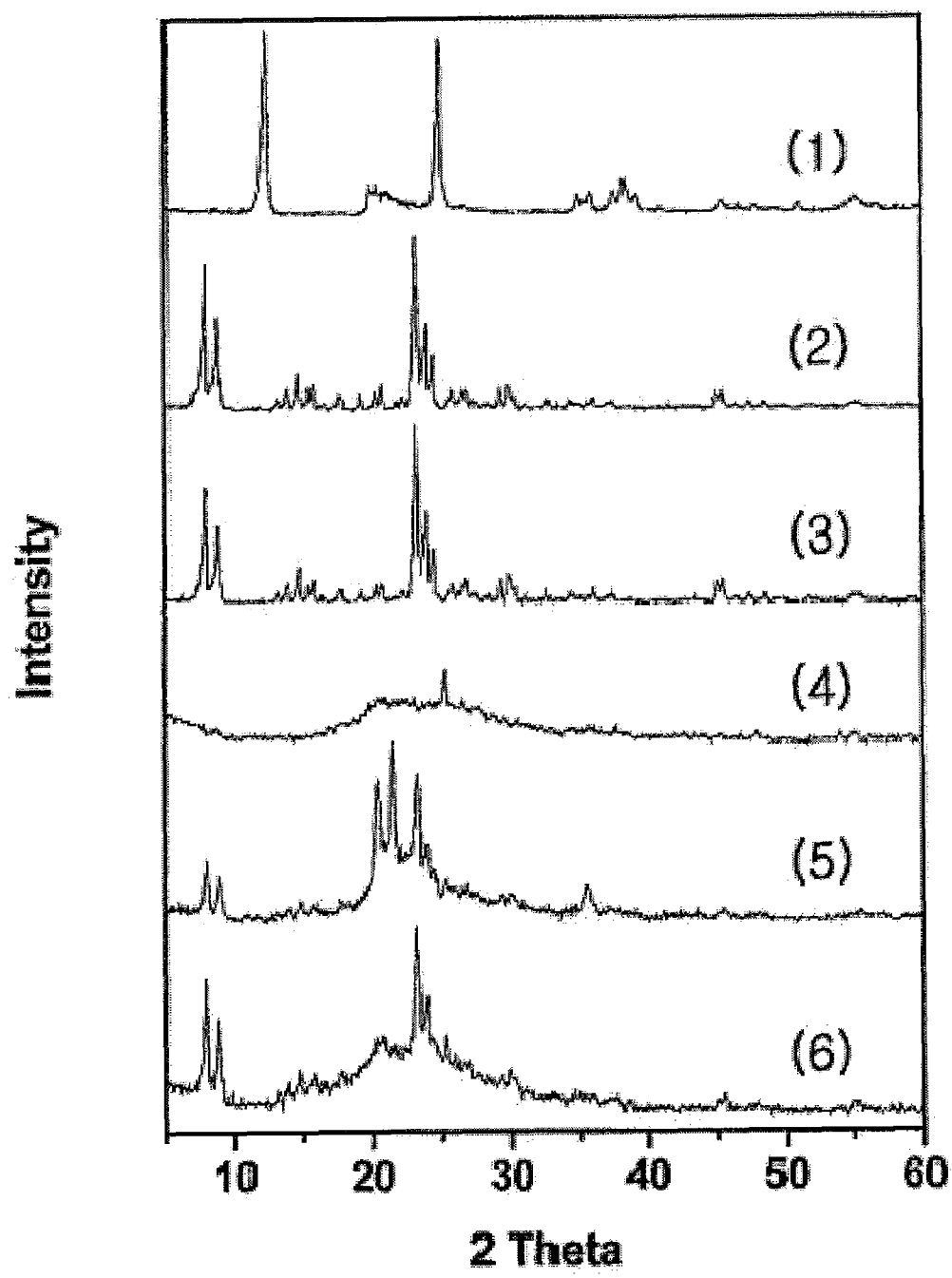
FIG. 3 illustrates XRD patterns of a layered compound, Kaolin (1), a pelletized catalyst prepared through heat treatment of HZSM-5 according to Comparative Example 8 (2), a pelletized catalyst prepared according to Comparative Example 3 (3), a pelletized catalyst prepared according to Comparative Example 1 (4), a pelletized catalyst prepared according to Comparative Example 6 (5), and a pelletized catalyst prepared according to Comparative Example 4 (6), respectively.

FIG. 3 illustrates XRD patterns of (1) a layered compound (Kaolin), (2) a pelletized catalyst produced according to Comparative Example 8, (3) a catalyst produced according to Comparative Example 3, (4) a catalyst produced according to Comparative Example 1, (5) a catalyst produced according to Comparative Example 6, and (6) a pelletized catalyst produced according to Comparative Example 4.

According to the drawing, the layered compound (1) is converted into an amorphous type (4) due to thermal instability of a structure thereof during a heat treatment process unlike HZSM-5 (2). The pelletized catalyst produced from the raw material exclusive of a specific component in comparison with the present invention, as shown in Comparative Example 3 (3) has an XRD pattern that is similar to that of ZSM-5. As shown in Comparative Example 4 (6) and Comparative Example 6 (5), the pelletized catalyst, which deviates from the present invention in the compositional range of the raw material, has the XRD pattern in which ZSM-5 and an amorphous layered compound having a destroyed structure are mixed with each other (6), and shows a pattern lacking crystallinity of the catalyst, or incorporation of third components. For example, if the raw material contains an excessive amount of specific component such as $Al_2O_3$ (5), third components generated by a solid state reaction of components other than a main component at high temperatures, co-exist within the resulting catalyst.

Method of Measuring Performance of the Catalyst

Figure 2:
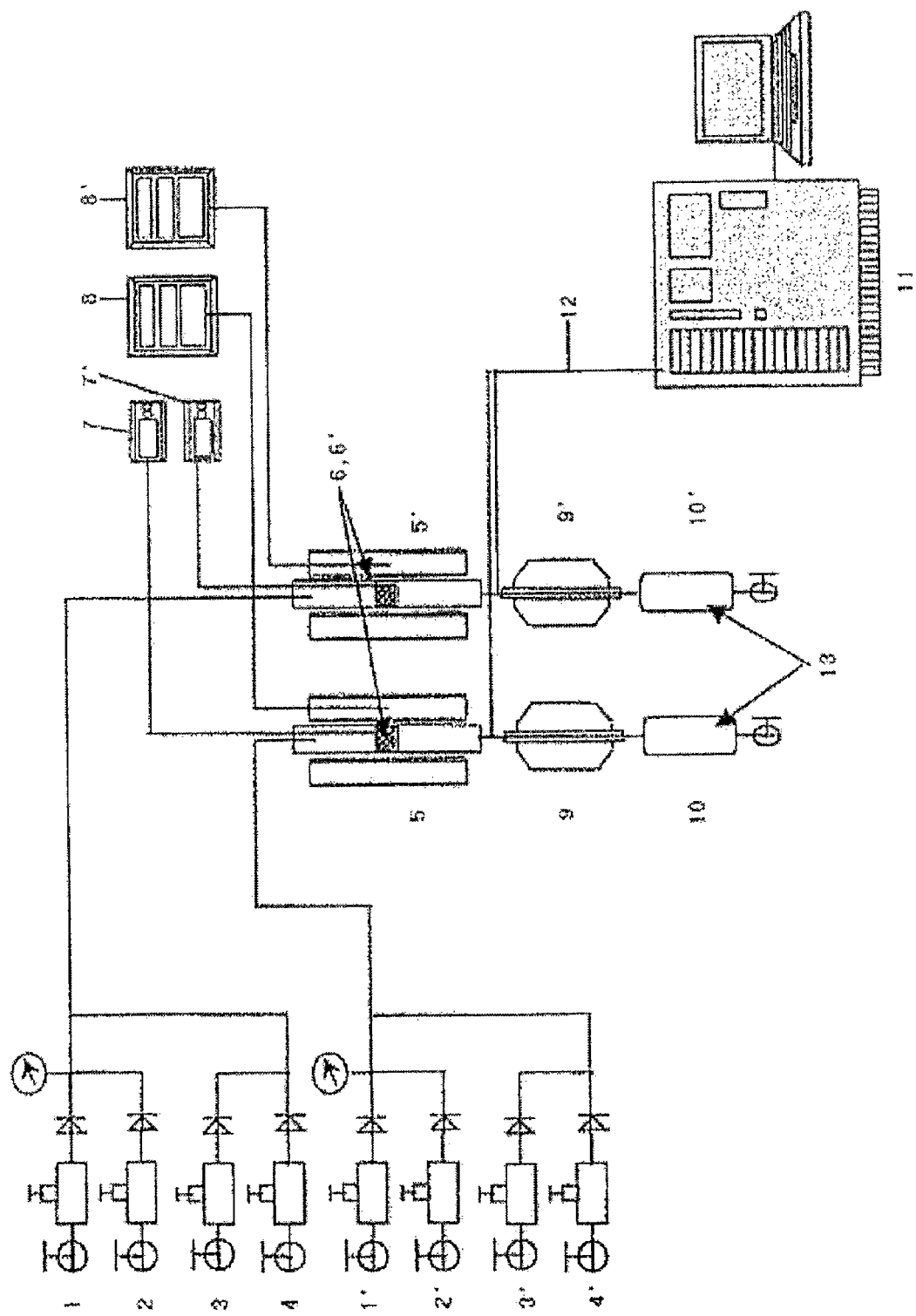
FIG. 2 schematically illustrates a system for measuring performances of catalysts prepared in accordance with Examples and Comparative Examples.

A system for measuring activity of the catalyst comprised a naphtha feeding device 4, a water feeding device 3, fixed bed reactors 5, 5', and an activity evaluation device as shown in FIG. 2, and were organically connected to each other. In this connection, naphthas which are specified in Table 2 were used as a feed. Naphthas and water which were fed using liquid injection pumps were mixed with each other while they passed through a preheater (not shown) at 300° C., mixed with He and $N_2$ which are supplied through helium feeders 2, 2' and nitrogen feeders 1, 1' at 6 Ml/min and 3 Ml/min, respectively, and then fed into the fixed bed reactors 5, 5'. The amounts and rates of gases were controlled using flow controllers (not shown). Each of the fixed bed reactors comprised an internal reactor and an external reactor. The external reactor was an Inconel reactor and had a length of 38 cm and an external diameter of 4.6 cm, while the internal reactor was made of stainless steel and had a length of 20 cm and an external diameter of 0.5 inches. The internal temperature of the reactor was indicated through temperature output units 7, 7', and reaction conditions were controlled using PID controllers 8, 8' (NP200 manufactured by Hanyoung Electronic Co., Ltd.).

Gas which was fed into the reactor sequentially passed through the internal reactor and the external reactor through which He flowed at 40 Ml/min, and the catalyst was packed in a lower part of the internal fixed bed reactor. The mixed gas was subjected to the reaction as it passed through catalytic beds 6, 6', and the gaseous products 12 after the reaction were quantitatively analyzed using a gas chromatograph 11 (model name: HP 6890N) in an online manner. Liquid products 13 passing through condensers 9, 9' were recovered in storage tanks 10, 10', and then quantitatively analyzed using a gas chromatograph (model name: DS 6200, not shown). An amount of catalyst used in the reaction was 0.5 g, amounts of naphthas and water supplied were each 0.5 g/h, and the reaction was conducted at 675° C.

Conversion efficiency, selectivity of light olefins (ethylene and propylene) in the reaction products, and a weight ratio of ethylene/propylene were evaluated for the catalysts produced according to Examples 1-3 and Comparative Examples 1-8, and the results are described in the following Table 4.

TABLE 3

| Composition of catalyst | Examples | | | Comparative examples | | | | | | | |
|---|---|---|---|---|---|---|---|---|---|---|---|
| (wt %) | 1 | 2 | 3 | 1 | 2 | 3 | 4 | 5 | 6 | 7 | 8 |
| HZSM-5 | 43.3 | 57.2 | 57.2 | — | — | 39.7 | 30.3 | 50 | 20.9 | 16.3 | 100 |
| Kaolin | 36.4 | 27.5 | 27.5 | 100 | 64.9 | 46.7 | 45.0 | 50 | 41.7 | 54.6 | — |
| $SiO_2$ | 13.7 | 10.3 | 10.3 | — | 24.3 | 10.5 | 17.0 | — | 8.4 | 20.5 | — |
| $P_2O_5$ | 2.9 | 2.2 | 2.2 | — | 5.2 | — | 3.6 | — | 16.3 | 4.4 | — |
| $Al_2O_3$ | 2.0 | 1.5 | 1.5 | — | 3.6 | 3.1 | 2.5 | — | 11.5 | 3.1 | — |
| $B_2O_3$ | 1.7 | 1.3 | 1.3 | — | 2.0 | — | 1.6 | — | 1.2 | 1.1 | — |

TABLE 4

| Distribution of products | Examples | | | Comparative examples | | | | | | | |
|---|---|---|---|---|---|---|---|---|---|---|---|
| | 1 | 2 | 3 | 1 | 2 | 3 | 4 | 5 | 6 | 7 | 8 |
| Type of full range naphthas | 1* | 1 | 2** | 1 | 1 | 1 | 1 | 1 | 1 | 1 | 1 |
| Conversion efficiency, wt % | 64.0 | 72.1 | 83.6 | 52.8 | 46.5 | 59.9 | 54.7 | 59.0 | 52.9 | 49.6 | 67.0 |
| $C_2$ | 23.3 | 28.2 | 23.8 | 16.4 | 14.4 | 20.1 | 18.3 | 20.7 | 16.7 | 13.8 | 25.7 |
| $C_3$ | 18.5 | 18.8 | 26.1 | 13.1 | 11.2 | 17.5 | 17.0 | 17.8 | 15.8 | 17.2 | 17.3 |
| $C_2$ and $C_3$ | 41.8 | 47.0 | 49.9 | 29.5 | 25.6 | 37.6 | 35.3 | 38.5 | 32.5 | 31.0 | 43.0 |
| $C_2/C_3$ | 1.26 | 1.50 | 0.91 | 1.25 | 1.29 | 1.15 | 1.08 | 1.16 | 1.06 | 0.81 | 1.49 |

*naphtha 1
**naphtha 2

From Table 4, it is confirmed that catalysts of Examples are different from those of Comparative Examples in catalytic activities. That is to say, the catalysts of Examples 1 and 2 have high conversion efficiency of about 64-72 wt % and simultaneously a total amount of ethylene and propylene of about 41-47 wt %, which means high selectivity (a weight ratio of ethylene/propylene is about 1.1-1.5).

On the other hand, the catalysts of Comparative Examples 1-3 and 5, which use the same feeds as in Examples 1 and 2, have conversion efficiency of about 46-60 wt % and a total amount of ethylene and propylene of 25-37 wt %. Particularly, the catalysts of Comparative Examples 4, 6, and 7, which include all of the components constituting the raw material of the present invention but have the compositional ratios deviating from that of the present invention, have conversion efficiency of about 49-54 wt % and a total amount of ethylene and propylene of about 31-35 wt %.

Furthermore, Example 3, which uses lighter full range naphthas as the feeds, has better conversion and selectivity to light olefins than those of Example 2. However, both Examples 2 and 3 show results that are higher than the desired level. Especially, considering that the present catalyst enables to employ full range naphthas, which are heavier than light naphthas used in the conventional steam cracking process, the present light olefin preparation is sufficiently competitive in terms of economic efficiency of the commercial process.

Meanwhile, when the catalyst consisting of only HZSM-5 is used (Comparative Example 8), the conversion is about 67 wt % and the total amount of ethylene and propylene is 43 wt %. This result can be considered to be similar to those of Examples 1 and 2, but since it is impossible to produce the pelletized catalyst using only HZSM-5, it is difficult to apply in practice.

Further, in the present invention, as shown in Examples 1 and 2, it is possible to assure as high catalytic performance as in the catalyst consisting only of HZSM-5 (Comparative Example 8) even though only about 50 wt % HZSM-5 is used, thus there is an economic advantage stemming from the use of less expensive raw materials. However, the pelletized catalyst, which employs simple combination of HZSM-5 and a layered compound each in an amount of 50 wt % as shown in Comparative Example 5, has the lowered conversion and selectivity to light olefins. The reason therefore is believed to be that it does not have the structure of the catalyst according to the present invention even though HZSM-5 as a main component is contained in an amount of 50% or more based on a total composition.

A porous solid acid catalyst according to the present invention has a crystalline structure which is converted by pillaring and solid state reactions and is quite different from structures of components constituting a raw material, particularly HZSM-5 and a layered compound. As a result, it is possible to assure excellent catalytic performance in the selective production of light olefins from hydrocarbons fraction, in particular, full range naphthas containing $C_{2-12}$ hydrocarbons. Further, the reactions involved in the preparation of the catalyst are simple, the price of raw materials for the catalyst is relatively less expensive, and it is possible to assure sufficient catalytic activity required to produce light olefins, even at a temperature lower than a reaction temperature required in the conventional steam cracking process. In addition, it is advantageous in that the present invention enables to use of relatively low-priced full range naphthas as feed for the production of light olefins.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A process for producing light olefins, comprising the steps of:

providing hydrocarbons fraction as a feed;

transferring the feed into a reaction zone comprising at least one reactor to react the feed in the presence of a porous solid acid catalyst comprising a product of a pillaring reaction and a solid state reaction through heat treatment of a raw material mixture, and has a crystalline structure represented by an X-ray diffraction pattern as follows:

| 2θ | Relative intensity |
|---|---|
| 7.899 | 81.4 |
| 8.760 | 48.1 |
| 14.76 | 15.3 |
| 19.92 | 15.2 |
| 20.36 | 21.2 |
| 23.06 | 100 |
| 23.88 | 59.7 |
| 24.36 | 24.5 |
| 25.60 | 15.3 |
| 25.82 | 18.4 |
| 26.60 | 22.2 |
| 26.86 | 20.8 |
| 29.90 | 22.5 |
| 45.00 | 17.5 |
| 45.48 | 17.4 | wherein the raw material mixture comprises 42.0-60.0 wt % HZSM-5 having Si/Al molar ratio of 15-300, 12.0-38.0 wt % layered compound, 1.0-20.0 wt % $Al_2O_3$, 1.0-4.0 wt % $P_2O_5$, 10.0-15.0 wt % $SiO_2$, and 0.5-2.5 wt % $B_2O_3$ based on an oxide form; and separating light olefins from an effluent of the reaction zone to recover light olefins.

2. The process as set forth in claim 1, wherein the feed comprises full range naphthas.

3. The process as set forth in claim 1, wherein the feed comprises full range naphthas having $C_{2-12}$ hydrocarbons.

4. The process as set forth in claim 2, wherein the full range naphthas have a total content of paraffin components in the range of 60-90 wt %, and a content of olefins in the range of 20 wt % or less.

5. The process as set forth in claim 3, further comprising the step of mixing remaining $C_{4-5}$ hydrocarbons after the light olefins are separated and recovered in the separating step, with the full range naphthas, so that a mixture of $C_{4-5}$ hydrocarbons and the full range naphthas are fed as the feed.

6. The process as set forth in claim 1, wherein the reactor is a fixed bed reactor or a fluidized bed reactor.

7. The process as set forth in claim 6, wherein, in a fixed bed reactor, the reaction is conducted under conditions of a reaction temperature of 500-750° C., a weight ratio of hydrocarbons/steam of 0.01-10, and a space velocity of 0.1-20 $h^{-1}$.

8. The process as set forth in claim 6, wherein, in a fluidized bed reactor, the reaction is conducted under conditions of a reaction temperature of 500-750° C., a weight ratio of hydrocarbons/steam of 0.01-10, a weight ratio of catalyst/hydrocarbons of 1-50, and a retention time of hydrocarbons of 0.1-600 sec.

9. The process as set forth in claim 1, wherein the light olefins in the effluent of the reaction zone has a total amount of ethylene and propylene of 40 wt % or more and a weight ratio of ethylene/propylene in the range of 0.5-1.5.

* * * * *

UNITED STATES PATENT AND TRADEMARK OFFICE
CERTIFICATE OF CORRECTION

PATENT NO. : 7,663,013 B2
APPLICATION NO. : 12/265729
DATED : February 16, 2010
INVENTOR(S) : Sun Choi et al.

It is certified that error appears in the above-identified patent and that said Letters Patent is hereby corrected as shown below:

Title Page

In Field (73), "Assignee":

Please add: --Korea Research Institute of Chemical Technology, Daejeon (KR)--

Signed and Sealed this
Fifteenth Day of March, 2011

David J. Kappos
*Director of the United States Patent and Trademark Office*